United States Patent
Kudlik

(10) Patent No.: US 11,617,878 B2
(45) Date of Patent: Apr. 4, 2023

(54) DIAGNOSTIC METRIC FOR CUMULATIVE PRESENCE OF SUCTION CONDITIONS

(71) Applicant: Medtronic, Inc., Minneapolis, MN (US)

(72) Inventor: D'Anne E. Kudlik, Saint Louis Park, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 129 days.

(21) Appl. No.: 17/119,399

(22) Filed: Dec. 11, 2020

(65) Prior Publication Data

US 2021/0220638 A1 Jul. 22, 2021

Related U.S. Application Data

(60) Provisional application No. 62/963,807, filed on Jan. 21, 2020.

(51) Int. Cl.
*A61M 60/592* (2021.01)
*A61M 60/178* (2021.01)

(52) U.S. Cl.
CPC ........ *A61M 60/592* (2021.01); *A61M 60/178* (2021.01); *A61M 2205/3334* (2013.01); *A61M 2250/00* (2013.01)

(58) Field of Classification Search
CPC ........ A61M 2205/3334; A61M 60/148; A61M 60/178; A61M 60/237; A61M 60/422; A61M 60/523; A61M 60/546; A61M 60/871
See application file for complete search history.

(56) References Cited

U.S. PATENT DOCUMENTS

| | | |
|---|---|---|
| 7,997,854 B2 | 8/2011 | LaRose et al. |
| 8,007,254 B2 | 8/2011 | LaRose et al. |
| 8,419,609 B2 | 4/2013 | Shambaugh, Jr. et al. |
| 8,512,013 B2 | 8/2013 | LaRose et al. |
| 9,492,601 B2 | 11/2016 | Casas et al. |
| 9,561,313 B2 | 2/2017 | Taskin |
| 9,623,161 B2 | 4/2017 | Medvedev et al. |
| 2014/0100413 A1* | 4/2014 | Casas ............. A61M 60/546 600/16 |
| 2018/0028738 A1 | 2/2018 | Brown et al. |
| 2019/0351116 A1 | 11/2019 | Kudlik |

FOREIGN PATENT DOCUMENTS

WO 2014197558 A2 12/2014

OTHER PUBLICATIONS

International Search Report and Written Opinion dated Apr. 9, 2021, for corresponding International Application No. PCT/US2020/066773; International Filing Date: Dec. 23, 2020 consisting of 9-pages.

* cited by examiner

*Primary Examiner* — Jon Eric C Morales
(74) *Attorney, Agent, or Firm* — Shumaker & Sieffert, P.A.

(57) ABSTRACT

A method of determining a cumulative presence of suction in a patient having an implanted blood pump including determining whether at least one suction event occurred during a predetermined time interval for a predetermined number of time intervals and determining the cumulative presence of suction by dividing a sum of a number of predetermined time intervals in which at least one suction event occurred by the predetermined number of time intervals.

20 Claims, 4 Drawing Sheets

DIAGNOSTIC METRIC FOR CUMULATIVE PRESENCE OF SUCTION CONDITIONS

CROSS-REFERENCE TO RELATED APPLICATION

This application claims the benefit of U.S. Application Ser. No. 62/963,807, filed Jan. 21, 2020

FIELD

The present technology is generally related to a method of determining a cumulative presence of suction in a patient with an implantable blood pump.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as ventricular assist device or "VAD." Where a VAD is used to assist the pumping action of the left ventricle, the device draws blood from the left ventricle of the heart and discharges the blood into the aorta at a predetermined flow rate.

However, if a VAD is operated at a flow rate in excess of the inflow rate of blood to the ventricle, the VAD creates a suction condition within the ventricle, wherein the ventricle is collapsed and essentially devoid of blood. This condition is undesirable. In this condition, the flow rate through the pump will decline rapidly. Likewise, if the intake or outlet of the pump is occluded, the flow rate will decline gradually. If the flow rate through the pump declines, either rapidly (e.g., as a result of suction condition) or gradually (e.g., as a result of an obstruction or occlusion) to the extent that the flow rate is insufficient, the device does provide sufficient circulatory assistance to the patient.

SUMMARY

The techniques of this disclosure generally relate to a method of determining a cumulative presence of suction in a patient with an implantable blood pump.

In one aspect, the present disclosure provides a method of determining a cumulative presence of suction in a patient having an implanted blood pump including determining whether at least one suction event occurred during a fixed time interval for a predetermined number of time intervals and calculating the cumulative presence of suction by dividing a sum of a number of fixed time intervals in which at least one suction event occurred by the predetermined number of time intervals.

In another aspect of this embodiment, the method occurs in real-time.

In another aspect of this embodiment, the predetermined time interval is approximately 0.25-5 seconds.

In another aspect of this embodiment, predetermined number of time intervals is between every 10 seconds to every 24 hours.

In another aspect of this embodiment, determining the cumulative presence of suction is performed continually.

In another aspect of this embodiment, the cumulative presence of suction is displayed in a log-file, controller, and/or monitor.

In another aspect of this embodiment, each of the predetermined number of time intervals are consecutive.

In another aspect of this embodiment, the implanted blood pump is communication with a controller to operate the blood pump, the controller being configured to determine a blood flow rate of the blood pump over time.

In one aspect, a method of operating an implanted blood pump includes determining a cumulative presence of suction, the cumulative presence of suction being determined by determining whether at least one suction event occurred during a predetermined time interval for a predetermined number of time intervals and dividing a sum of a number of predetermined time intervals in which at least one suction event occurred by the predetermined number of time intervals and generating an alert alerting if the determined cumulative presence of suction increases above a predetermined cumulative presence of suction threshold.

In another aspect of this embodiment, the predetermined time interval is approximately 0.25-5 seconds.

In another aspect of this embodiment, the predetermined number of time intervals is between every 10 seconds to every 24 hours.

In another aspect of this embodiment, determining the cumulative presence of suction is performed continually.

In another aspect of this embodiment, the cumulative presence of suction is displayed in a log-file, controller, and/or monitor.

In another aspect of this embodiment, each of the predetermined number of time intervals are consecutive.

In another aspect of this embodiment, the implanted blood pump is communication with a controller to operate the blood pump, the controller being configured to determine a blood flow rate of the blood pump over time.

In another aspect of this embodiment, determining in the cumulative presence of suction occurs in real time.

In one aspect, a control circuit for operation an implantable blood pump, the control circuit being configured to: determine a cumulative presence of suction, the cumulative presence of suction being determined by: determining whether at least one suction event occurred during a predetermined time interval for a predetermined number of time intervals and dividing a sum of a number of predetermined time intervals in which at least one suction event occurred by the predetermined number of time intervals. An alert is generated if the determined cumulative presence of suction increases above a predetermined cumulative presence of suction threshold.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
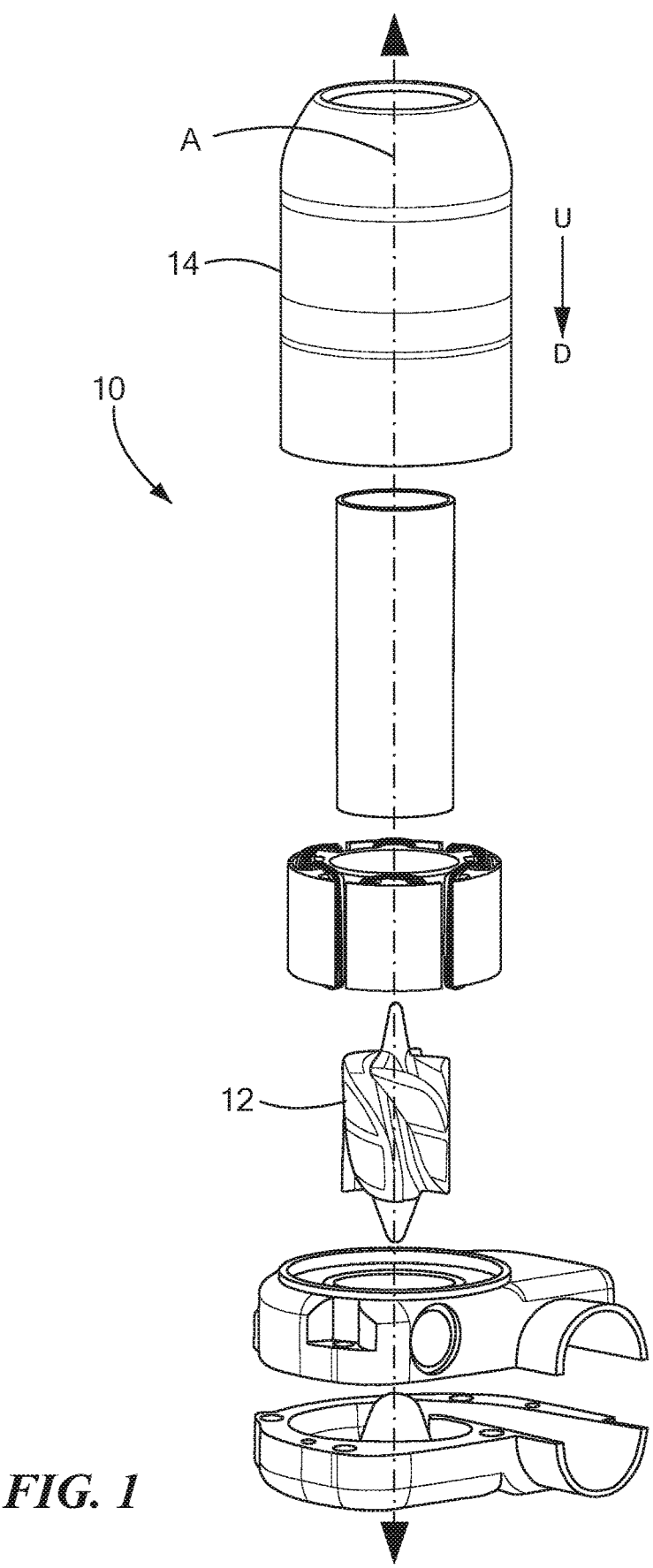
FIG. 1 is a disassembled view of an implantable blood pump.

Referring now to the drawings in which like reference designators refer to like elements there is shown in FIG. 1 a disassembled view of an exemplary implantable blood pump 10 configured to be implanted within a patient, such as a human or animal patient. The blood pump 10 may be, without limitation, the HVAD® Pump or the MVAD® Pump, having a movable element, such as an impeller 12 or a rotor, configured to rotate and impel blood from the heart to the rest of the body. The HVAD® Pump is further discussed in U.S. Pat. Nos. 7,997,854 and 8,512,013, the disclosures of which are incorporated herein by reference in the entirety. The MVAD® Pump is further discussed in U.S. Pat. Nos. 8,007,254, 8,419,609, and 9,561,313, the disclosures of which are incorporated herein by reference in the entirety.

Figure 2:
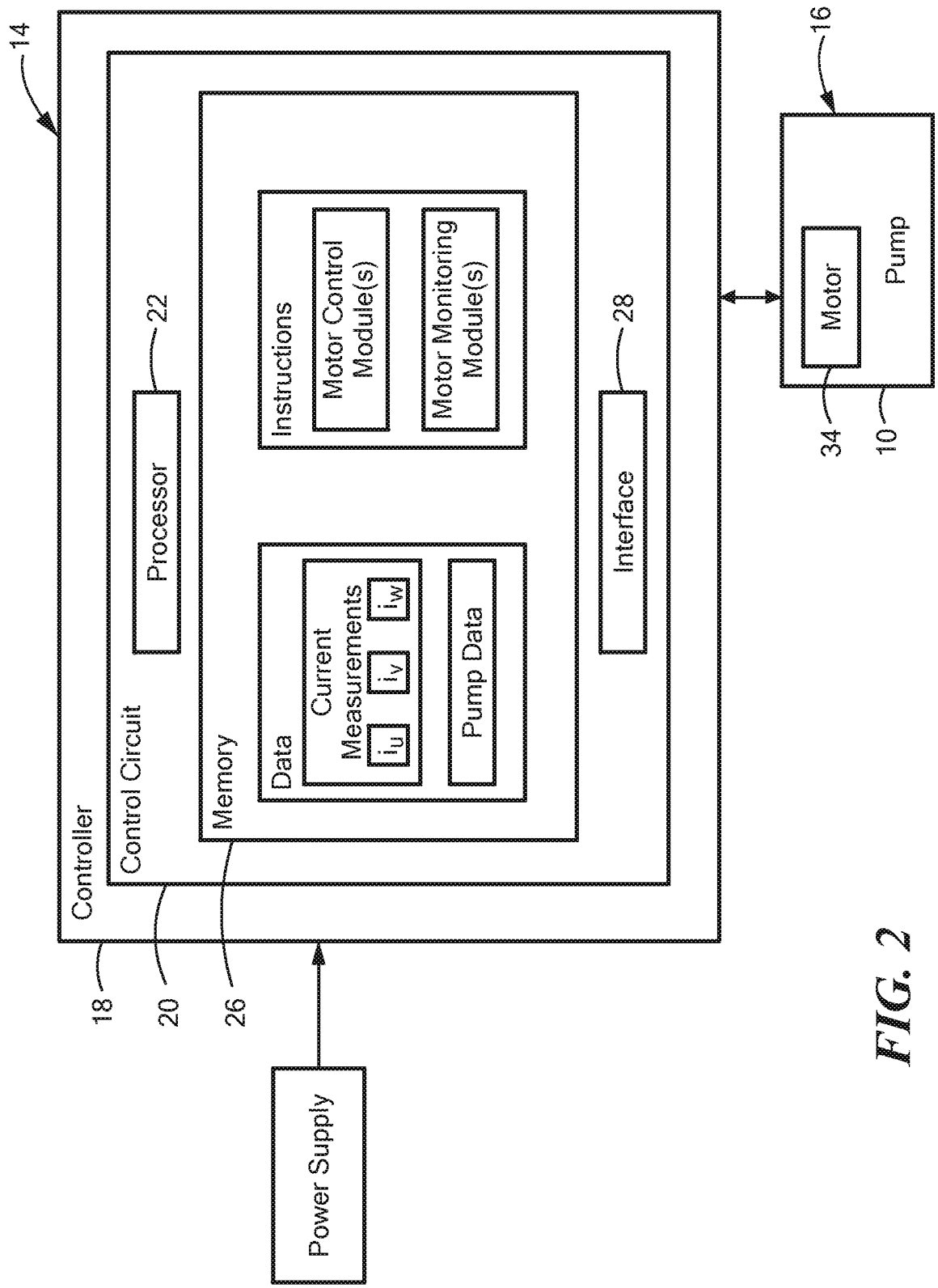
FIG. 2 is a block diagram of a system for controlling a pump speed of the blood pump of FIG. 1.

FIG. 2 is a block diagram of an exemplary system 14 for controlling a pump speed and/or other operations of the implantable blood pump 10 when the blood pump 10 is in communication with the system 14. The blood pump 10 includes a motor 16 therein and may be a separate component or form part of the system 14. In one example, the system 14 includes a controller 18 having a control circuit 20 and a processor 22 including processing circuitry 24 configured to perform the operations of the blood pump 10. The system 14 may also include a memory 26 and an interface 28, the memory 26 being configured to store information accessible by the processor 22, including instructions executable by the processing circuitry 24 and/or data that may be retrieved, manipulated or stored by the processor 22. Such instructions and/or data include that which is used to control the pump speed.

Figure 3:
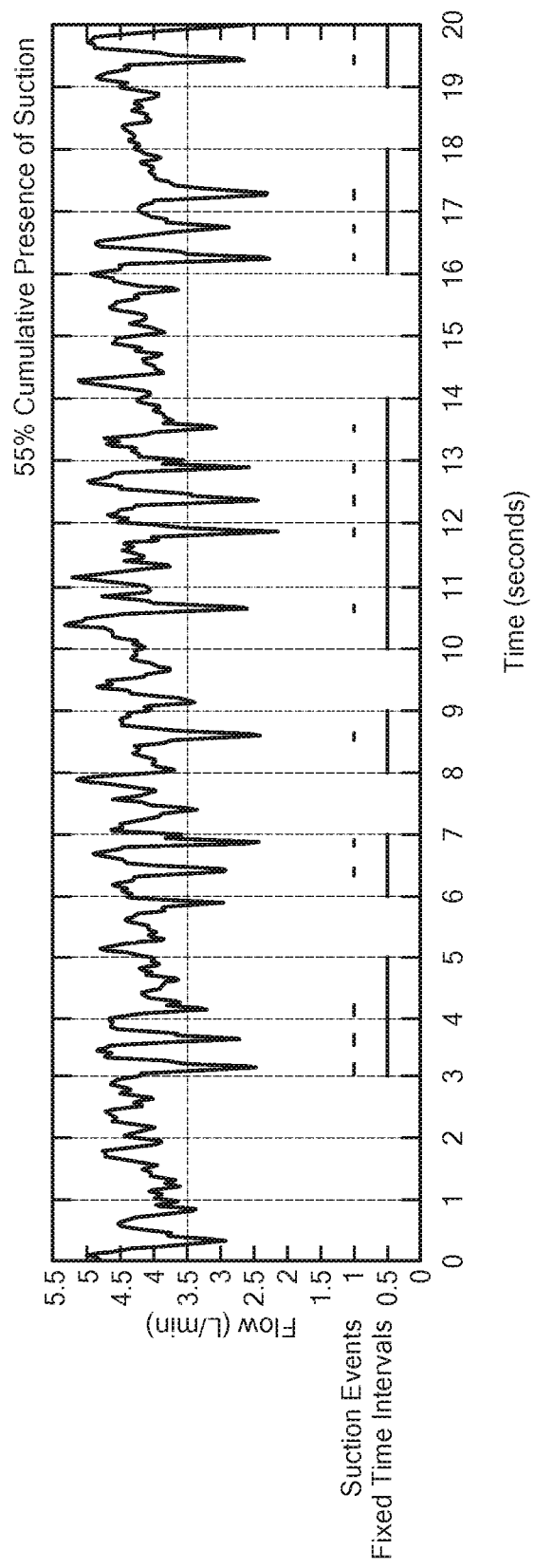
FIG. 3 is a log file showing a cumulative presence of suction on a patient with an implantable blood pump.

Referring now to FIG. 3 in which an exemplary graph 30 showing how the cumulative presence of suction is calculated is shown. The control circuit 20 of the controller 18 is configured to measure and monitor a parameter of the blood pump 10, for example, current, and correlate that into a measure of flow rate over time. The control circuit 20 is further configured to identify at least one suction events 32, which are characterized by a brief period of low blood flow corresponding to when the inflow element of the blood pump 12 contacts a wall of the heart and briefly interrupting blood flow. Such algorithms, for example, those disclosed by U.S. Pat. No. 9,492,601, the entirety of which is expressly incorporated by reference herein, may be employed by the control circuit 20 to determine the present or absence of suction. The suction events 32 are identified by the broken lines and labeled suction events shown in FIG. 3.

Figure 4:
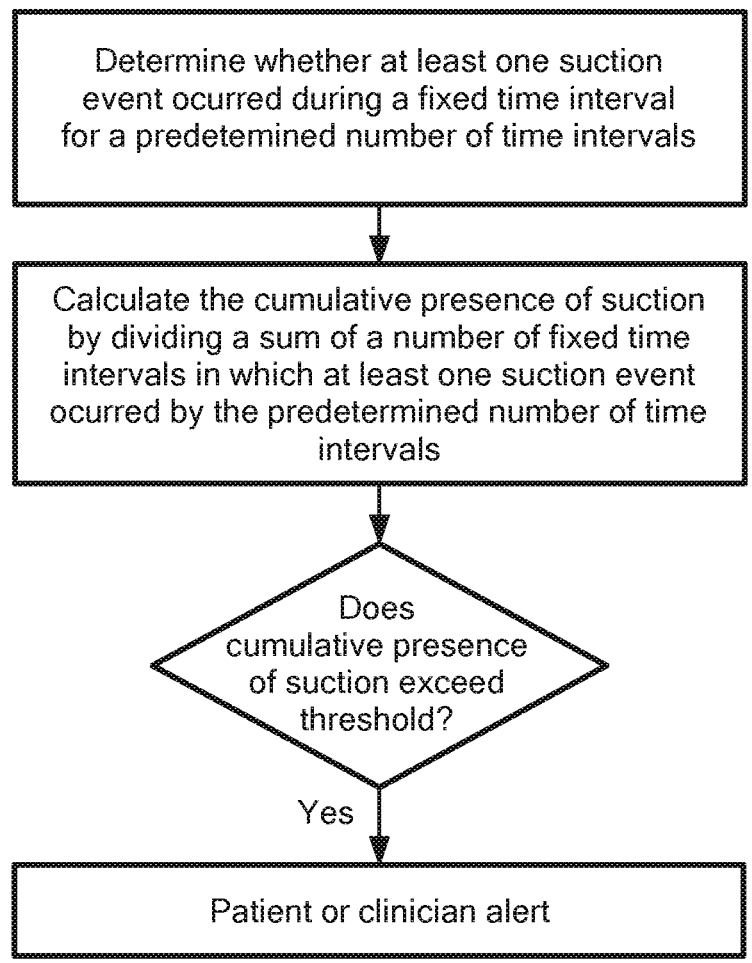
FIG. 4 is a flow chart illustrating a method of determining a patient's cumulative presence of suction.

Referring now to FIGS. 3-4, the control circuit 20 is configured to determine whether the least one suction event 32 occurred during a predetermined time interval 34 for a predetermined number of time intervals 36. In particular, the control circuit 20 will determine whether the suction event 32 occurred during a one second interval, or any time duration interval, for example 0.25-5 seconds, and score that interval as including a suction event 32 (Step 100). For example, as shown in FIG. 3, although two suction events 32 occurred during the 3-4 second time interval, the control circuit 20 identifies that time as including at least one section event 32, regardless of how many suction events 32 occurred during that time period. Thus, the time interval between 3-4 second is identified by, for example, a solid red line, to indicate the presence of at least one suction event 32. The control circuit 20 may then sum up the total number of intervals that include at least one suction event for the predetermined number of time intervals (Step 102). For example, 20 time intervals 36 of one second are shown in FIG. 3 and of those 20 one second intervals, eleven include at least one suction event 32. In other configurations the time intervals 36 may range from every 10 seconds to every 24 hours. The control circuit 20 may then divide a sum of the number of predetermined time intervals 34 in which at least one suction event 32 occurred by the predetermined number of time intervals 36. For example, in the graph 30 shown in FIG. 3, eleven intervals include at least suction event 32. The control circuit 20 calculates 11/20 to determine a cumulative presence of suction of 55%.

The control circuit 20 may determine the cumulative presence of suction in real-time and/or may determine the cumulative presence of suction based on a graph 30 produced at, for example, a clinician's office. For example, the cumulative presence of suction may be displayed in a log-file, monitor, or controller. In an exemplary configuration, the determination of the cumulative presence of suction is made in real-time and is continual and/or periodic. For example, the cumulative presence of suction may be determined continuously for each continuing 20 second window. Alternatively, the cumulative presence of suction may be determined in, for example, consecutive 20 second windows. In one configuration, if the determined cumulative presence of suction exceeds a predetermined cumulative presence of suction threshold, for example, 60-80% an alert may be generated indicating the presence of suction which may be forward directly to the clinician for further diagnostics and potential interventions.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of determining a cumulative presence of suction in a patient having an implanted blood pump, the method comprising:
   determining whether at least one suction event occurred during a predetermined time interval for a predetermined number of time intervals; and
   determining the cumulative presence of suction by dividing a sum of a number of predetermined time intervals in which one or more suction events occurred by the predetermined number of time intervals.

2. The method of claim 1, wherein the method occurs in real-time.

3. The method of claim 1, further including generating a log-file displaying the cumulative presence of suction.

4. The method of claim 1, wherein the predetermined time interval is approximately 0.25-5 seconds.

5. The method of claim 1, wherein the predetermined number of time intervals is every 10 seconds to every 24 hours.

6. The method of claim 5, wherein determining the cumulative presence of suction is performed continually.

7. The method of claim 1, wherein each of the predetermined number of time intervals are consecutive.

8. The method of claim 1, further comprising determining a blood flow rate of the blood pump over time, wherein determining whether the at least one suction event occurred during the predetermined time interval comprises determining whether the at least one suction event occurred during the predetermined time interval based on the blood flow rate.

9. A method of operating an implanted blood pump, the method comprising:
   determining a cumulative presence of suction, the cumulative presence of suction being determined by:
      determining whether at least one suction event occurred during a predetermined time interval for a predetermined number of time intervals; and
      dividing a sum of a number of predetermined time intervals in which one or more suction events occurred by the predetermined number of time intervals; and
   generating an alert if the determined cumulative presence of suction increases above a predetermined cumulative presence of suction threshold.

10. The method of claim 9, wherein the predetermined time interval is approximately 0.2-5 seconds.

11. The method of claim 9, wherein the predetermined number of time intervals is every 10 seconds to every 24 hours.

12. The method of claim 9, wherein determining the cumulative presence of suction is performed continually.

13. The method of claim 9, wherein the cumulative presence of suction is displayed in a log-file, controller, or monitor.

14. The method of claim 9, wherein each of the predetermined number of time intervals are consecutive.

15. The method of claim 9, further comprising determining a blood flow rate of the blood pump over time, wherein determining whether the at least one suction event occurred during the predetermined time interval comprises determining whether the at least one suction event occurred during the predetermined time interval based on the blood flow rate.

16. The method of claim 11, wherein determining in the cumulative presence of suction occurs in real time.

17. A control circuit for operation an implantable blood pump, the control circuit being configured to:
   determine a cumulative presence of suction, the cumulative presence of suction being determined by:
      determining whether at least one suction event occurred during a predetermined time interval for a predetermined number of time intervals; and
      dividing a sum of a number of predetermined time intervals in which oen or more suction events occurred by the predetermined number of time intervals; and
   generate an alert if the determined cumulative presence of suction increases above a predetermined cumulative presence of suction threshold.

18. The control circuit of claim 17, wherein the control circuit is configured to determine the cumulative presence of suction and generate the alert in real-time.

19. The control circuit of claim 17, wherein the predetermined number of time intervals are consecutive.

20. The control circuit of claim 17, wherein the control circuit is further configured to determine a blood flow rate of the blood pump over time and determine whether the at least one suction event occurred during the predetermined time interval based on the blood flow rate.

* * * * *